US007984711B2

(12) United States Patent
Schipper et al.

(10) Patent No.: US 7,984,711 B2
(45) Date of Patent: Jul. 26, 2011

(54) CARRYING SYSTEM WITH BREATHING APPARATUS

(75) Inventors: David Schipper, Salt Lake City, UT (US); Peter Wilkening, Salt Lake City, UT (US); David Narajowski, Park City, UT (US); Paul Terry, Park City, UT (US); Thomas Laakso, Park City, UT (US); David Mellon, Park City, UT (US)

(73) Assignee: Black Diamond Equipment, Ltd., Salt Lake City, UT (US)

( * ) Notice: Subject to any disclaimer, the term of this patent is extended or adjusted under 35 U.S.C. 154(b) by 617 days.

(21) Appl. No.: 11/287,692

(22) Filed: Nov. 28, 2005

(65) Prior Publication Data

US 2007/0119455 A1 May 31, 2007

(51) Int. Cl.
*A61M 15/00* (2006.01)
*A62B 7/00* (2006.01)

(52) U.S. Cl. .................................................. 128/202.13

(58) Field of Classification Search ............. 128/202.13, 128/204.17, 204.18, 205.12, 205.27, 205.28; 2/9

See application file for complete search history.

(56) References Cited

U.S. PATENT DOCUMENTS 3,496,703 A * 2/1970 MacLeod et al. ............... 96/296
4,062,359 A * 12/1977 Geaghan .................. 128/204.17
4,365,628 A * 12/1982 Hodel ...................... 128/205.12
4,683,869 A * 8/1987 Wilcox ......................... 126/204
4,739,913 A * 4/1988 Moore .......................... 224/643
4,768,235 A * 9/1988 Webster ............................ 2/205
4,901,370 A * 2/1990 Suda ................................ 2/457
4,964,405 A * 10/1990 Arnoth ..................... 128/205.17
5,003,634 A * 4/1991 Brinkman ........................... 2/46
5,114,059 A * 5/1992 Thatcher .................... 224/148.5
5,370,113 A * 12/1994 Parsons .................... 128/205.22
5,400,934 A * 3/1995 Ducros ...................... 224/148.2
5,490,501 A * 2/1996 Crowley .................. 128/204.17
6,412,482 B1 * 7/2002 Rowe ....................... 128/204.18
6,510,974 B2 * 1/2003 Willingham et al. ......... 224/657

(Continued)

FOREIGN PATENT DOCUMENTS

DE 2326850 12/1974

(Continued)

*Primary Examiner* — Justine Yu
*Assistant Examiner* — Colin W Stuart
(74) *Attorney, Agent, or Firm* — Trent Baker; Baker & Associates PLLC

(57) ABSTRACT

The present invention relates to carrying systems including packs and bags. One embodiment of the present invention is directed at a carrying system that includes a snow breathing apparatus. The system includes a carrying cavity, an attachment system, and a snow breathing apparatus. The carrying cavity is a partially enclosed region that is capable of storing items for transportation. The carrying cavity may further include a shell, a lid, a sealing system, a compression system, etc. The attachment system is coupled to an external surface of the carrying cavity to facilitate a removable coupling between the carrying cavity and a user. The attachment system may include two arm straps, a shoulder strap, a hip belt, a belt receiver, etc. The snow breathing apparatus is a device that enables breathing in a snow encapsulated breathing space in which breathing may otherwise be restricted. The snow breathing apparatus is coupled to the carrying cavity in a manner that prevents interference with carried items but maintains functionality of the breathing apparatus.

18 Claims, 5 Drawing Sheets

U.S. PATENT DOCUMENTS

| | | | | |
|---|---|---|---|---|
| 6,722,533 | B2 * | 4/2004 | Skillern | 222/175 |
| 6,807,964 | B1 * | 10/2004 | Ruddy | 128/204.17 |
| 2001/0052532 | A1 * | 12/2001 | Perez et al. | 224/575 |
| 2004/0089301 | A1 * | 5/2004 | Choi et al. | 128/203.29 |
| 2010/0132702 | A1 * | 6/2010 | Ogilvie | 128/201.22 |

FOREIGN PATENT DOCUMENTS

| | | | |
|---|---|---|---|
| DE | 2326850 | A1 | 12/1974 |
| DE | 9314670 | U1 | 1/1994 |

* cited by examiner

CARRYING SYSTEM WITH BREATHING APPARATUS

FIELD OF THE INVENTION

The invention generally relates to carrying systems including packs and bags. In particular, the invention relates to a carrying system that includes a breathing apparatus.

BACKGROUND OF THE INVENTION

Packs are used to transport materials from one location to another or to provide access to particular items that are needed during travel. The term "packs" is meant to include backpacks, hip-packs, messenger bags, belt packs, etc. Packs also enable a user to perform activities while they are carrying items. People typically carry or transport loose materials with their hands; however this method of carrying impedes their abilities to perform tasks or activities. For example, a user's skiing ability would be dramatically affected if they were carrying water, extra clothing, and a map in their hands. Whereas, if these same items are stored in a pack, the user's ability to ski is only minimally affected by the items.

Breathing apparatuses are used to facilitate assisted breathing in situations in which breathing would otherwise be compromised. One type of breathing apparatus allows users to avoid carbon dioxide contamination in confined breathing situations. These apparatuses include one or more one-way air valves that direct exhaled carbon dioxide to a location that is independent of the inhaled oxygen, thereby preventing contamination. This type of apparatus has been particularly useful in extending the time in which an avalanche victim is able to breathe while trapped under the snow. Although snow can prevent mobility, it contains a large amount of oxygen that can be utilized to sustain a burial victim for a long period of time. By extending the time in which a burial victim is able to breathe, rescuers are given sufficient time to locate the victim and remove the superficial snow.

One of the problems with existing breathing apparatuses is that they are inconvenient to use. Because clothing affects or obstructs air-flow, the breathing apparatus must be worn on the outside of all articles of clothing. This necessitates multiple restrictions on the manner in which breathing apparatuses can be utilized. First, the breathing apparatus must be positioned and/or configured so as to not interfere with any other external items including but not limited to packs, harnesses, etc. Second, the breathing apparatus must be removed if the user wishes to add or remove clothing layers. Third, the breathing apparatus must be easily adjustable to accommodate the exterior dimensions of a user in a variety of activities or circumstances. These restrictions often result in either misuse of a breathing apparatus or avoidance.

Therefore, there is a need in the industry for a breathing apparatus system that overcomes the restrictions of current breathing apparatuses.

SUMMARY

The present invention relates to carrying systems including packs and bags. One embodiment of the present invention is directed at a carrying system that includes a snow breathing apparatus. The system includes a carrying cavity, an attachment system, and a snow breathing apparatus. The carrying cavity is a partially enclosed region that is capable of storing items for transportation. The carrying cavity may further include a shell, a lid, a sealing system, a compression system, etc. The attachment system is coupled to an external surface of the carrying cavity to facilitate a removable coupling between the carrying cavity and a user. The attachment system may include two arm straps, a shoulder strap, a hip belt, a belt receiver, etc. The snow breathing apparatus is a device that enables breathing in a snow encapsulated breathing space in which breathing may otherwise be restricted. The snow breathing apparatus is coupled to the carrying cavity in a manner that prevents interference with carried items but maintains functionality of the breathing apparatus.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1B:
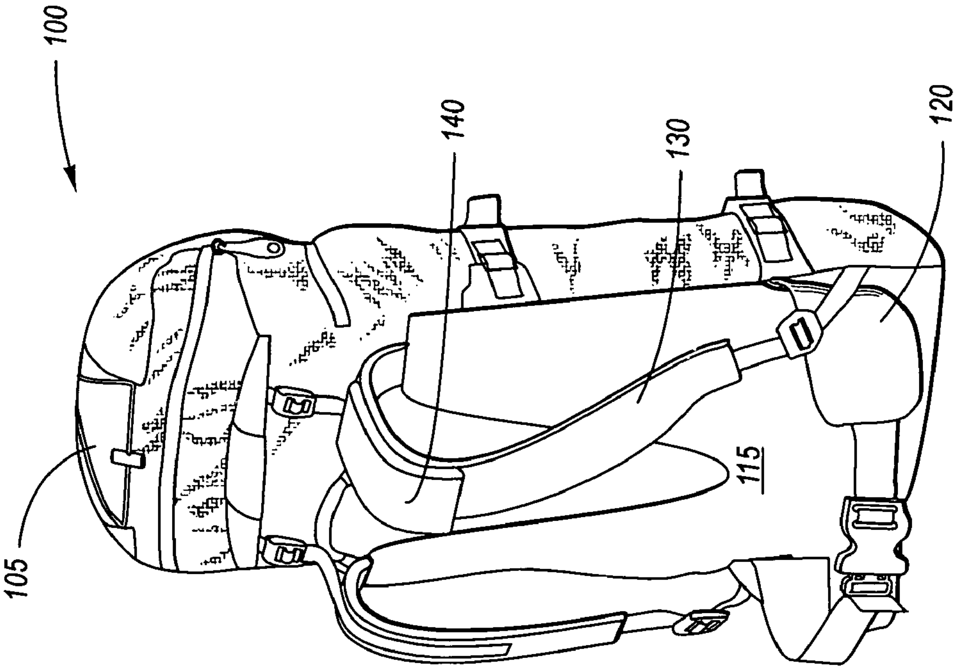
FIG. 1B illustrates a perspective front view of the carrying system with a breathing apparatus illustrated in FIG. 1A, wherein the breathing apparatus is in a deactivated state.

The present invention relates to carrying systems including packs and bags. One embodiment of the present invention is directed at a carrying system that includes a snow breathing apparatus. The system includes a carrying cavity, an attachment system, and a snow breathing apparatus. The carrying cavity is a partially enclosed region that is capable of storing items for transportation. The carrying cavity may further include a shell, a lid, a sealing system, a compression system, etc. The attachment system is coupled to an external surface of the carrying cavity to facilitate a removable coupling between the carrying cavity and a user. The attachment system may include two arm straps, a shoulder strap, a hip belt, a belt receiver, etc. The snow breathing apparatus is a device that enables breathing in a snow encapsulated breathing space in which breathing may otherwise be restricted. The snow breathing apparatus is coupled to the carrying cavity in a manner that prevents interference with carried items but maintains functionality of the breathing apparatus. Also, while embodiments of the present invention are directed at carrying systems including packs and bags, it will be appreciated that the teachings of the present invention could be applied to other areas.

The following terms are defined as follows:

Carrying cavity—A partially enclosed region which can be used to house or store items including but not limited to a pack, a bag, a backpack, a hip-pack, a duffel, a purse, a belt w/ pouch, a shoulder bag, a messenger bag, a chest bag, etc. A carrying cavity may be shaped in many partially enclosed configurations including a cylindrical shape in which one of the openings is closed. The carrying cavity may include a closure system for selectively enclosing the partially enclosed region. An alternative carrying cavity may include two similarly shaped partially enclosed regions coupled together with a selective closure system such as a zipper. The zipper closure system could provide access to the partially enclosed regions in an opened state or selectively enclose the partially enclosed regions from all exterior access in a closed state.

Attachment system—A system for attaching a carrying cavity to an individual to facilitate transportation of the carrying cavity without the constant use of both of a user's hands. Attachment systems include shoulder straps, hip straps, neck straps, etc.

Snow breathing apparatus—an apparatus configured to enable breathing in a snow encapsulated breathing space in which breathing may otherwise be compromised. For example, a valve-based breathing direction system that forces exhaled carbon dioxide to be exhaled to a location positionally independent from the location at which air is inhaled.

Gravity based load-bearing forces—forces induced on an individual as a result of carried items. For example, the downward pressure exerted by a backpack as a result of items stored in the backpack.

Snow encapsulated breathing space—a space in which snow in part obstructs or impedes normal breathing in some manner. For example, an avalanche victim may be buried in a confined space between snow and other materials including rock, dirt, and debris. Since the space is confined, breathing will be impaired due to the limited oxygen in the surrounding materials. In the cited example, breathing may also be impaired by the necessity of breathing in exhaled carbon dioxide.

Figure 1A:
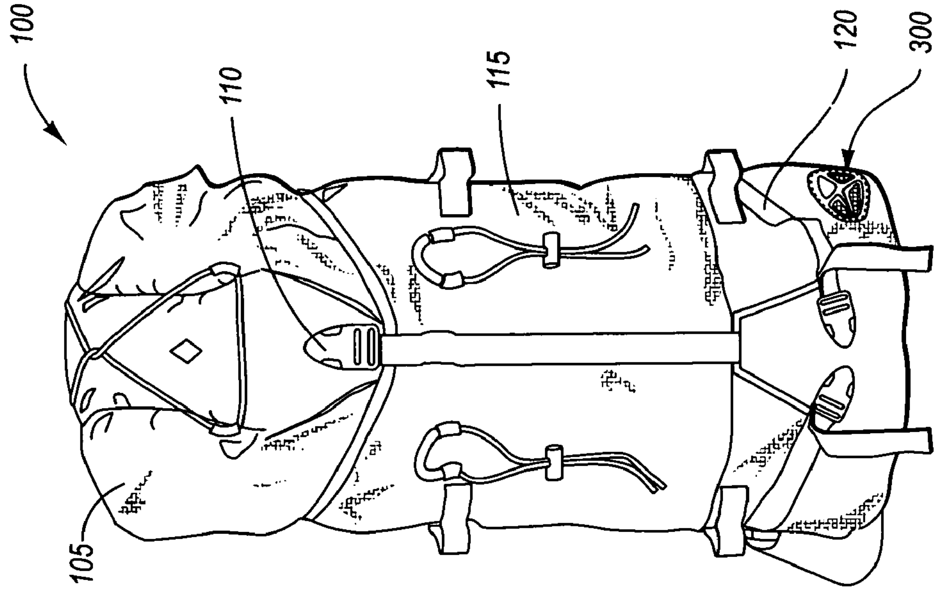
FIG. 1A illustrates a perspective back view of a carrying system with a breathing apparatus in accordance with one embodiment of the present invention.

Reference is initially made to FIGS. 1A and 1B, which illustrates a carrying system with a breathing apparatus in accordance with one embodiment of the present invention, designated generally at 100. The carrying system includes a carrying cavity 115, a closure system 105, 110, and an attachment system 120, 130. The carrying cavity 115 or body of the carrying system is a hollow region with an upper open end and a lower closed end. The upper open end is covered by the closure system including a lid 105 and a lid attachment 110. The lid 105 and lid attachment 110 can be selectively opened to allow access to an inner partially enclosed region of the carrying cavity 115. The inner partially enclosed region provides a location in which items may be stored for transportation or protection. The carrying cavity 115 is composed of a flexible supportive material including but not limited to nylon, canvas, Cordura, etc. Additional attachments or accessories may be disposed on the outer or inner portions of the carrying cavity 115 including but not limited to pouches, clasps, buckles, pockets, daisy chains, flaps, bladder sleeves, etc. An exit manifold 300 is disposed on a lower portion of the carrying cavity 115 as illustrated. The exit manifold 300 will be described in more detail with reference to FIGS. 2-3. In the illustrated embodiment, the exit manifold 300 is integrated into the carrying cavity 115 in a manner that provides the capability for air flow between the interior partially enclosed region and the exterior of the carrying cavity 115.

The illustrated attachment system 120, 130 includes two shoulder straps 130 and a set of hip straps 140. The shoulder straps 130 are designed to loop over a user's shoulder to partially transfer the weight of the stored items and carrying cavity 115. This transfer of weight enables the user to carry weights that may otherwise be unmanageable or uncomfortable. In addition, the hip straps 140 are designed to further transfer weight of the stored items and the carrying cavity 115. Various adjustments may be made to the hip straps 120 and the shoulder straps 130 to accommodate the size of the user, the terrain over which the carrying system 100 is carried, and the weight of the stored items in the carrying cavity 115. Various other attachment systems and/or attachment system accessories may be utilized and remain consistent with the present invention. The left shoulder strap (from a user's perspective) further includes a selectively closeable pouch 140. The interior of the pouch 140 provides an access channel to the partially enclosed region of the carrying cavity 115. A breathing apparatus 200 is positioned in the pouch 140 and extends down through the partially enclosed region to the exit manifold 300 as will be described in more detail with reference to FIGS. 2-3.

Figure 2:
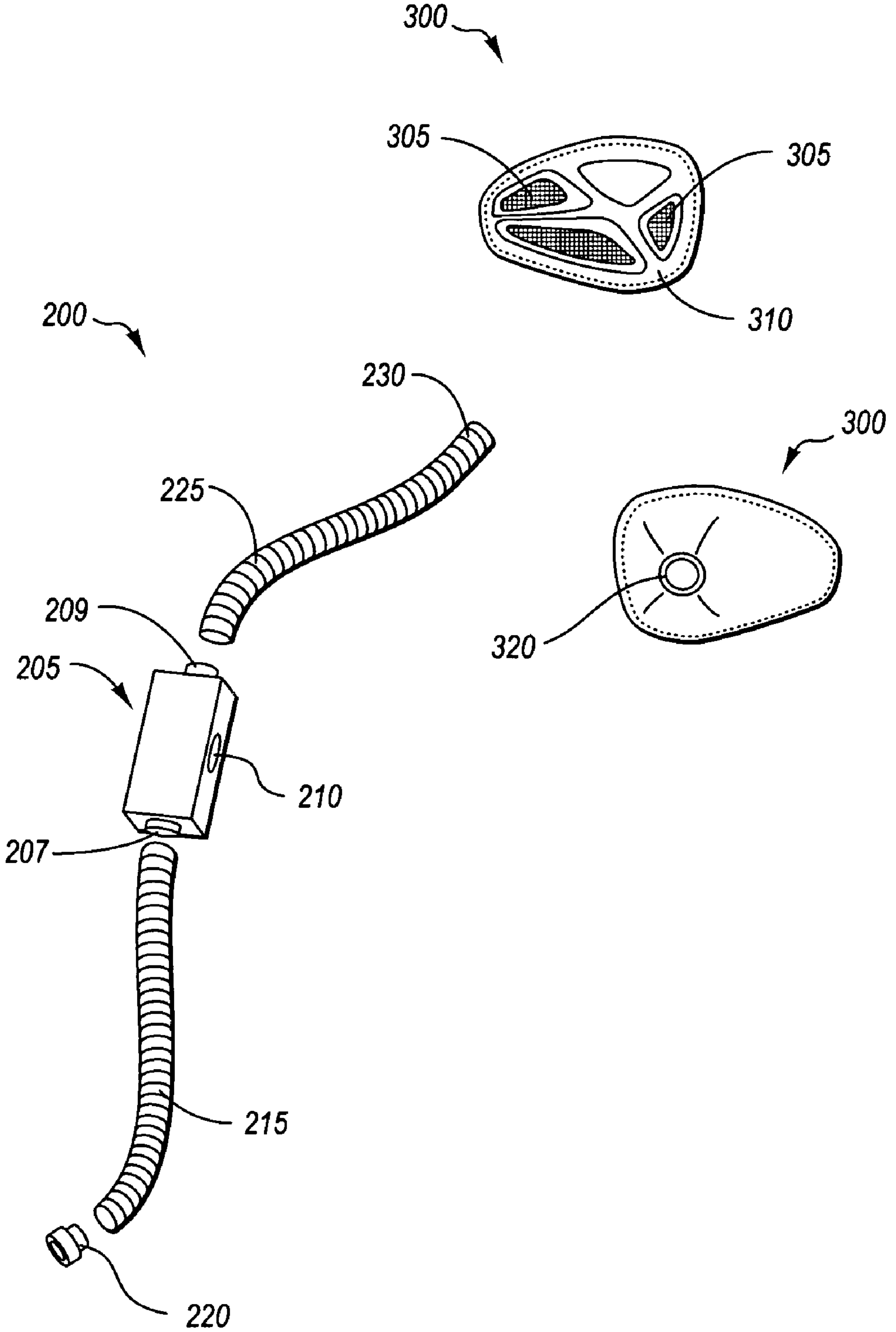
FIG. 2 illustrates an exploded view of one type of breathing apparatus for use with the present invention.

Reference is next made to FIG. 2, which illustrates an exploded view of one type of breathing apparatus for use with the present invention, designated generally at 200. The illustrated breathing apparatus is a snow breathing apparatus that enables breathing in a snow encapsulated breathing space. This is particularly useful in an emergency snow related breathing situation such as when an individual is buried under the snow by an avalanche. Breathing in a confined space is particular dangerous because of the potential to inhale previously exhaled carbon dioxide. The illustrated breathing apparatus minimizes the potential for breathing exhaled carbon dioxide by separating the location at which air is inhaled from the location at which carbon dioxide is exhaled. However, the breathing apparatus must be properly activated and utilized in order to provide the benefits described above. Various existing breathing apparatuses are problematic in that they are not convenient to use and therefore often inaccessible in an emergency situation. The illustrated breathing apparatus is configured to be incorporated into a carrying system 100 to provide a convenient deployment system. In particular, the breathing apparatus 200 includes a mouthpiece 220, a mouthpiece tube 215, a valve member 205, an exhale tube 225, and an exhale port 230. In addition, an exit manifold 300 is illustrated in both a front and back configuration.

The illustrated mouthpiece 220 is a single manufactured member that includes an airway channel and a bite region to facilitate a comfortable air coupling with a user's mouth. The mouthpiece tube 215 is coupled to the mouthpiece 220 in a substantially air tight manner such that air-flow through the airway channel of the mouthpiece is able to transmit through a corresponding interior region of the mouthpiece tube 220. The mouthpiece tube 220 is an elongated cylindrical tube composed of a flexible yet puncture resistant material including but not limited to a plastic composite. The mouthpiece tube 220 may also include telescopic type functionality such that it can be extended and retracted to adjust in length. The mouthpiece tube 220 preferably includes two tubular members in which one of the tubular members is inserted within the other. The use of two interested tubular members enables an increase in memory type flexibility properties that are typically associated with a thicker walled tubular member. In addition, the dual tubular member system increases the resistance of the mouthpiece tube 215 to crushing that may otherwise restrict or impede airflow. The mouthpiece tube 215 is also coupled to the valve member 205 via a mouthpiece coupler 207.

The valve member 205 includes an intake opening 210 that is configured such that when a user inhales, air is drawn in through the intake opening 210 and transmitted up through the mouthpiece tube 215 and mouthpiece 220 to the user's mouth. A one-way valve is disposed on an interior portion of the valve member 205 to only air to be drawn in through the intake opening while restricting air from being exhaled out the intake opening. The one-way valve utilized in the illustrated embodiment is a duckbill reed type valve but any one-way air-flow restriction valve may be utilized. The valve member 205 also includes a similar one-way valve coupled to an exit coupler 209 and configured such that all exhaled air from the mouthpiece tube 215 is directed out the exhale coupler 209 and transmitted through the exhalation tube 225. Various other valve type configurations may be utilized to provide the same effect while remaining consistent with the teachings of the present invention.

The exhale tube 225 is also an elongated flexible cylindrical member with similar properties to the mouthpiece tube 215. The exhale tube 225 is coupled to the valve member 205 in a substantially air-tight manner via the exhale coupler 209. The exhale port 230 is also coupled to the exit manifold 300 in a manner to transmit exhaled air. The exhale tube 225 must be routed and disposed such that the location of the exhale port 230 is positionally independent of the intake opening 210 to prevent the inhalation of exhaled carbon dioxide.

In order to activate the breathing apparatus 200, the mouthpiece 220 must be coupled to a user's mouth such that all inhalations and exhalations are transmitted through the mouthpiece 220, the mouthpiece tube 215, and into the valve member 205. The valve member 205 distinguishes between inhalation and exhalations with the use of two one-way valves. If air is inhaled through the mouthpiece, the valve member 205 allows air to drawn in through the intake opening 210 and up to the mouthpiece. If air or carbon dioxide is exhaled, the valve member 205 directs the exhaled air out the exhale tube 225 and exhale port 230.

Figure 3:
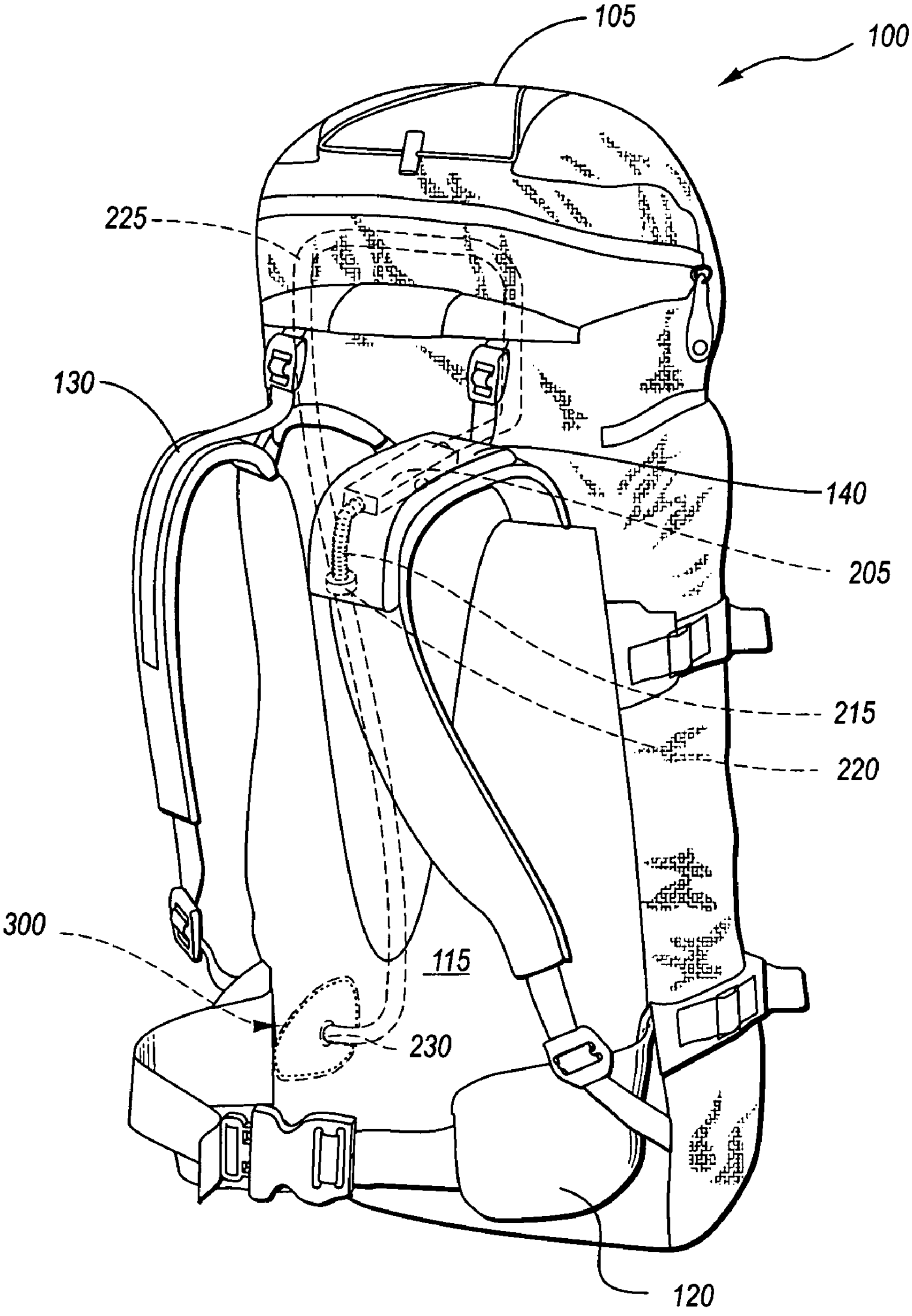
FIG. 3 illustrates a perspective front view of the carrying system with a breathing apparatus illustrated in FIGS. 1A and 1B wherein the breathing apparatus is shown in phantom to illustrate its position with respect to the carrying system.

The exit manifold 300 is configured to be coupled to the liner of a carrying system in the manner illustrated in FIGS. 1A and 3. The exit manifold 300 includes an opening 320 that is coupled to a plurality of exterior openings 305 on an outer surface 310 of the exit manifold 300. Therefore, carbon dioxide that is input into the opening 320 will be transmitted out the exterior openings 305. The exterior openings 305 further include some form of mesh or screen protection that allow gas transmission but prevent clogging due to snow or debris. In addition, the exterior surface 310 of the exit manifold is three dimensionally shaped to prevent blockage of gas transmission in the event of the exterior surface 310 being disposed over a surface such as a rock or dirt. The coupling between the exhale port 230 and the opening 320 is configured to be releasable to allow a user to selectively disengage the breathing apparatus 200 from the exit manifold 300.

Reference is next made to FIG. 3, which illustrates a perspective view of the carrying system 100 illustrated in FIGS. 1A and 1B wherein the breathing apparatus 200 illustrated in FIG. 2 is shown in phantom to illustrate its position with respect to the carrying system. The carrying system 100 includes a lid 105, a carrying cavity 115, a pair of shoulder straps 130, and a pair of hip straps 120. The breathing apparatus 200 is disposed in the partially enclosed region of the carrying cavity 115 in the manner shown. The breathing apparatus 200 is positioned so as to not interfere with the carrying systems 100 ability to comfortably transport items stored in the partially enclosed region. This is accomplished through a novel routing and coupling system described below.

A portion of the breathing apparatus 200 is disposed in a selectively closeable pouch 140 disposed on the left shoulder strap 130. The pouch 140 can be selectively opened via some form of closure system including but not limited to a zipper or Velcro to provide access to the breathing apparatus 200. The pouch 140 protects the breathing apparatus from debris and damage when not in use. When opened, a user is able to telescopically extend the mouthpiece 220 and mouthpiece tube 215 out of the pouch and position it in their mouth. The memory type flexibility properties of the mouthpiece tube 215 can also be used to shape the mouthpiece tube 215 in a manner that allows for rapid engagement of the mouthpiece 220 with a user's mouth. The valve member 205 remains substantially fixed in the pouch 140 such that the position of the intake opening remains constant. The valve member 205 and pouch 140 are positioned on the shoulder strap 130 in a manner such that gravity based load-bearing forces are not transferred onto the valve member 205 in an uncomfortable manner. The optimal positioning for the valve member 205 on the shoulder strap has been determined to be such that it is above or behind the clavicle and trapezius muscle connection point on the shoulder strap. In addition to preventing discomfort, the positioning of the valve member 205 must be sufficiently close to the user's mouth to avoid stagnant breathing in the mouthpiece tube 215. If the distance between the mouthpiece 220 and the valve member 205 is too large, there is a potential to inhale previously exhaled carbon dioxide. Therefore, the location of the valve member 205, mouthpiece 220, mouthpiece tube 215, and pouch 140 relative to the remainder of the carrying system 100 is an optimization of the various factors affecting the performance of the breathing apparatus 200 and the carrying system 100 in general to carry stored items.

The breathing apparatus 200 is also integrated within the carrying system 100 in a manner that allows the breathing apparatus 200 to be removed. The couplings between the exhale port 230 and the exit manifold 300, the exhale tube 225 and the valve member 205, and coupling between the mouthpiece tube 215 and the mouthpiece 220 are all releasable to allow for disassembly of the breathing apparatus 200 and disengagement from the carrying system 100. In addition, the positional couplings between the breathing apparatus 200 and the carrying cavity 115 are also releasable to allow for removal of the breathing apparatus 200 from the carrying cavity 115. The valve member 205, mouthpiece tube 215, and mouthpiece 220 can be disengaged from the exhale tube 225 and removed from the pouch 140. The exhale tube 225 can be removed from any type of flaps, pouches, or pockets which orient it along the side of the carrying cavity 115 in the manner shown. Once disengaged from the exit manifold 300, the exhale tube 225 may be removed through the top opening of the carrying cavity 115. The illustrated exit manifold is integrated into the carrying cavity 115 and cannot be remove. However, some form of plug, cap or protection system may be used to cover the internal opening 320 of the exit manifold 300 to prevent items or debris inside the carrying cavity 115 from entering the exit manifold 300.

Figure 4:
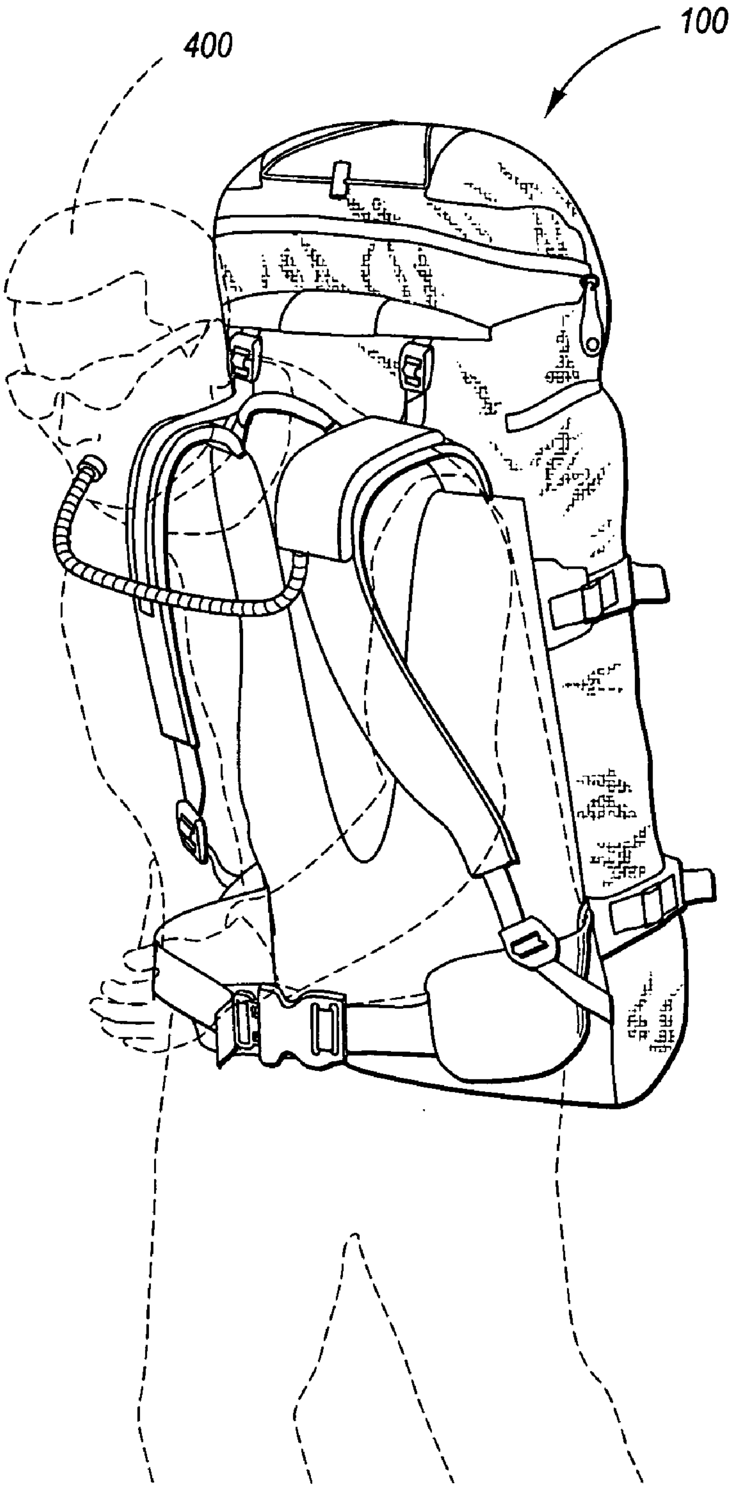
FIG. 4 illustrates a perspective view of a carrying system in accordance with the present invention in an activated state on a user.
Figure 5:
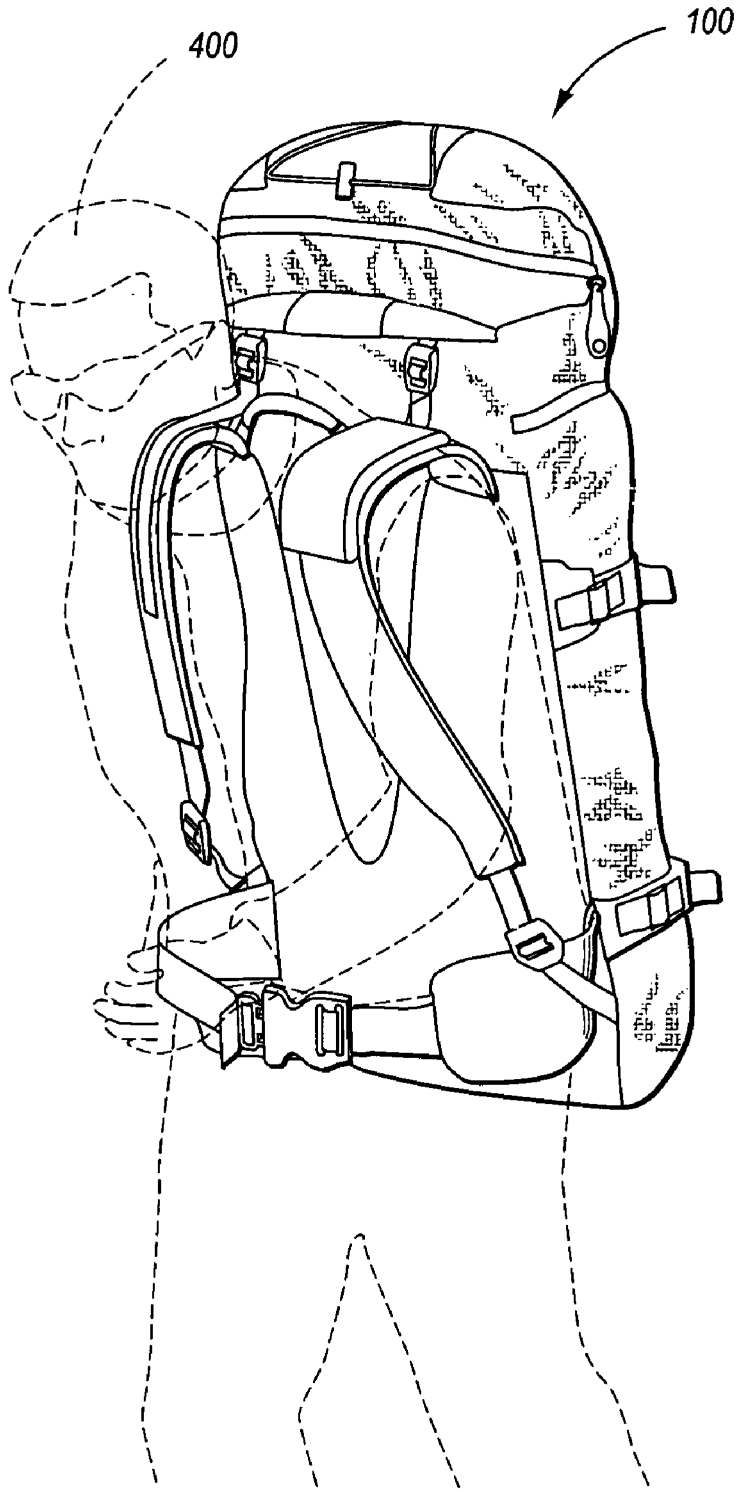
FIG. 5 illustrates a perspective view of a carrying system in accordance with the present invention in a deactivated state on a user.

Reference is next made to FIGS. 4 and 5, which illustrates a carrying system in accordance with the present invention in activated and deactivated respective states on a user. FIG. 4 illustrates a user 400 with a backpack type carrying system 100 consistent with the present invention, wherein the carrying system 100 includes a breathing apparatus 200. The user 400 is able to engage in various athletic events while coupled to the carrying system 100 thereby allowing for the transportation of various items without substantial restriction or discomfort. The breathing apparatus 200 is illustrated in a disengaged configuration in FIG. 5 because it is disposed within the pouch 140 on the shoulder strap 130. In order to engage the breathing apparatus 200, the user must open the pouch 140 and extend the mouthpiece 220 to their mouth such that inhalations and exhalations are properly transmitted through the mouthpiece 220 and into the remainder of the breathing apparatus 200. Likewise, the user 400 may disengage the breathing apparatus 200 by removing it from their mouth. The user 400 may also collapse the mouthpiece 220 back into the pouch 140 to protect the breathing apparatus 200 and prevent inteferenc.

Thus, as discussed herein, the present invention relates to carrying systems including packs and bags. In particular, the invention relates to a carrying system that includes a snow breathing apparatus. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A carrying system with a snow breathing apparatus comprising:

a carrying cavity including a partially enclosed region, wherein the partially enclosed region further includes an external surface, an internal surface, and an opening;

an attachment system coupled to the external surface of the carrying cavity to facilitate removeably coupling the carrying cavity to a user; and a snow breathing apparatus configured to enable breathing in a snow encapsulated breathing space in which breathing may otherwise be compromised, wherein the snow breathing apparatus is substantially housed within and coupled to an internal surface of the carrying cavity occupying less than fifty percent of the partially enclosed region volume, wherein the snow breathing apparatus is configured to enable ambient air to be inhaled from a location positionally independent from the location at which carbon dioxide is exhaled, and wherein the opening of the partially enclosed region is independent of the snow breathing apparatus and provides external access.

2. The carrying system of claim 1, wherein the carrying cavity further includes a closure system configured to selectively cover the opening so as to completely enclose the partially enclosed region.

3. The carrying system of claim 1, wherein the carrying cavity and attachment system are shaped in a manner consistent with a conventional backpack.

4. The carrying system of claim 1, wherein the attachment system includes two shoulder straps configured to releasably loop over the shoulders of a user.

5. The carrying system of claim 1, wherein the snow breathing apparatus further includes:

an inhalation member that permits air to be drawn in to the snow breathing apparatus from a first region of snow;

an inhalation valve that allows air to be drawn in through the inhalation member at the first region but prevents exhalation out the inhalation member;

an exhalation member that permits exhaled carbon dioxide to be exhaled into a second region of snow, wherein the second region of snow is positionally independent from the first region of snow; and an exhalation valve that allows carbon dioxide to be exhaled out through the exhalation member at the second region but prevents inhalation through the exhalation member.

6. The carrying system of claim 5, wherein the snow breathing apparatus is coupled to the carrying cavity in a manner to maximize the separation between the inhalation member and the exhalation member thereby minimizing the potential for inhalation of exhaled carbon dioxide.

7. The carrying system of claim 5, wherein the snow breathing apparatus includes a mouthpiece coupled to the inhalation member and the exhalation member via the inhalation valve and the exhalation valve respectively such that inhaled air is drawn in through the inhalation member only and exhaled carbon dioxide is exhaled out the exhalation member only.

8. The carrying system of claim 7, wherein the attachment system includes two shoulder straps, and wherein the mouthpiece is coupled to one of the shoulder straps in a enclosable manner which includes an enclosed state and a deployed state.

9. The carrying system of claim 7, wherein the mouthpiece is disposed in a selectively enclosable pouch on the attachment system.

10. The carrying system of claim 5, wherein the snow breathing apparatus is coupled to the attachment system in a manner that prevents gravity based load bearing forces from being transferred to a user through a rigid portion of the snow breathing apparatus in an uncomfortable manner.

11. The carrying system of claim 1, wherein the snow breathing apparatus is releasably coupled to the carrying cavity and the attachment system such that the carrying cavity and the attachment system can be used to transport items independent of the snow breathing apparatus.

12. The carrying system of claim 1, wherein the snow breathing apparatus includes an exit manifold integrated through the internal and external surface of the carrying cavity, and wherein the exit manifold is three dimensionally shaped to allow air flow even if disposed over a flat surface.

13. A method for breathing in a confined snow encapsulate space comprising the acts of:

engaging a carrying system including a partially enclosed region, wherein the carrying system includes a snow breathing apparatus housed substantially within the partially enclosed region occupying less than fifty percent of the partially enclosed region volume, and wherein the engagement of the carrying system includes engaging an attachment system coupled to an external surface of the partially enclosed region;

opening a selectively closeable region to facilitate activation of the snow breathing apparatus, wherein the selectively closeable region is independent of an opening to the partially enclosed region which provides external access; and breathing through the snow breathing apparatus such that ambient air is inhaled from a location positionally independent from the location at which carbon dioxide is exhaled.

14. The method of claim 13, wherein the snow breathing apparatus further includes:

an inhalation member that permits air to be drawn in to the snow breathing apparatus from a first region of the snow;

an inhalation valve that allows air to be drawn in through the inhalation member at the first region but prevents exhalation out the inhalation member;

an exhalation member that permits exhaled carbon dioxide to be exhaled into a second region of the snow; and an exhalation valve that allows carbon dioxide to be exhaled out through the exhalation member at the second region but prevents inhalation through the exhalation member.

15. The method of claim 13, wherein the act of opening a selectively closeable region to facilitate activation of the snow breathing apparatus includes unzipping a pouch disposed on a shoulder strap of the carrying system.

16. The method of claim 13, wherein the act of breathing through the snow breathing apparatus includes engaging a mouthpiece such that all inhalations and exhalations are transmitted through the mouthpiece.

17. A method for integrating a snow breathing apparatus into a carrying system including the acts of:

providing a carrying system including a carrying cavity and an attachment system, wherein the carrying cavity includes a partially enclosed region, and wherein the attachment system is coupled to the external surface of the carrying cavity and configured to be removeably coupled to a user to allow for transportation;

providing a snow breathing apparatus that includes an inhalation member, an exhalation member, and a mouthpiece, wherein the snow breathing apparatus is configured such that, when activated, ambient air is inhaled from a location positionally independent from the location at which carbon dioxide is exhaled;

positioning the exhalation member on a lower region of the carrying cavity;

routing the snow breathing apparatus through a selectively enclosed interior pouch substantially within the partially enclosed region occupying less than fifty percent of the partially enclosed region volume;

positioning the mouthpiece in a selectively enclosed pouch disposed on the attachment system to facilitate rapid deployment, wherein the selectively enclosed pouch is independent of an opening of the partially enclosed region which provides external access; and positioning the inhalation member on the attachment system to maximize separation between the inhalation member and the exhalation member.

18. The method of claim 17, wherein act of positioning the exhalation member on a lower region of the carrying cavity includes releasably coupling an exit manifold on a lower region of the carrying cavity that provides an airway through the carrying cavity.

* * * * *